US00PP11504P

United States Patent [19]

Abell

[11] Patent Number: Plant 11,504

[45] Date of Patent: Sep. 5, 2000

[54] BRACHYCOME PLANT NAMED 'COMPACT AMETHYST'

[75] Inventor: Peter George Abell, Blaxland, Australia

[73] Assignee: University of Sydney Plant Breeding Institute, Cobbitty, Cobbitty, Australia

[21] Appl. No.: 09/195,598

[22] Filed: Nov. 19, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Michelle Kizilkaya
*Attorney, Agent, or Firm*—C. A. Whealy

[57] ABSTRACT

A new and distinct cultivar of Brachycome plant named 'Compact Amethyst', characterized by its compact and outwardly spreading growth habit; very freely branching plant habit, plants do not require pinching; large number of inflorescences that are about 1.8 cm in diameter, with dark lavender ray florets; long peduncles that hold inflorescences above or beyond the foliage; and good weather tolerance.

2 Drawing Sheets

BACKGROUND OF THE INVENTION

The present invention relates to a new and distinct cultivar of Brachycome plant, botanically known as Brachycome hybrid and referred to by the cultivar name 'Compact Amethyst'.

The new Brachycome is a product of a planned breeding program conducted by the Inventor in Cobbitty, New South Wales, Australia. The objective of the program is to create new compact Brachycome cultivars that flower early, are easy to propagate, have uniform plant habit, are tolerant to temperature extremes, and have inflorescences with attractive ray floret color.

The new Brachycome originated from a cross by the Inventor in 1994 of the Brachycome hybrid cultivar 'Billabong Bright Eyes' (disclosed in U.S. Plant Pat. No. 10,192), as the female, or seed, parent with the nonpatented Brachycome hybrid cultivar 'Break O Day' as the male, or pollen, parent. The cultivar 'Compact Amethyst' was discovered and selected by the Inventor in 1996 as a flowering plant within the progeny of the stated cross in a controlled environment in Cobbitty, New South Wales, Australia.

Asexual reproduction of the new Brachycome by terminal cuttings taken in a controlled environment in Cobbitty, New South Wales, Australia, has shown that the unique features of this new Brachycome are stable and are reproduced true to type in successive generations.

SUMMARY OF THE INVENTION

The new Brachycome has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Compact Amethyst' and distinguish 'Compact Amethyst' as a new and distinct cultivar:

1. Compact and outwardly spreading growth habit.
2. Very freely branching plant habit, plants do not require pinching.
3. Very floriferous with numerous inflorescences that are about 1.8 cm in diameter, with dark lavender ray florets.
4. Long peduncles that hold inflorescences above or beyond the foliage.
5. Good weather tolerance.

Compared to plants of the female parent, the cultivar 'Billabong Bright Eyes', plants of the new Brachycome are larger, more vigorous, have larger inflorescences and darker ray floret color.

Compared to plants of the male parent, the cultivar 'Break O Day', plants of the new Brachycome are more spreading, have lighter foliage color and paler ray floret color.

Plants of the new Brachycome can be compared to nonpatented Brachycome hybrid cultivar 'Amethyst'. However, in side-by-side comparisons conducted in Cobbitty, New South Wales, Australia, plants of the new Brachycome are more spreading, are more basally and freely branching and are more floriferous than plants of the cultivar 'Amethyst'.

BRIEF DESCRIPTION OF THE PHOTOGRAPHS

The accompanying colored photographs illustrate the overall appearance of the new Brachycome, showing the colors as true as it is reasonably possible to obtain in colored reproductions of this type.

The photograph on the first sheet comprises a top perspective view of a typical potted plant of 'Compact Amethyst'.

The top of the photograph on the second sheet comprises a close-up view of typical developing inflorescences of 'Compact Amethyst' from bud stage (left) to fully opened inflorescence (right).

The bottom of the photograph on the second sheet comprises a close-up view of typical developing leaves 'Compact Amethyst' from bud stage (right) to fully developed leaf (left). Floret and foliage colors in the photographs may appear different from the actual colors due to light reflectance.

DETAILED BOTANICAL DESCRIPTION

The following observations, measurements, values, and comparisons describe plants grown in Bonsall, Calif., under outdoor full-sun conditions with day temperatures ranging from 18 to 35° C., night temperatures ranging from 13 to 18° C. Color references are made to The Royal Horticultural Society Colour Chart except where general terms of ordinary dictionary significance are used.

Botanical classification: Brachycome hybrid cultivar 'Compact Amethyst'.

Parentage:

*Male or pollen parent.*—Brachycome hybrid cultivar 'Break O Day', not patented.

*Female or seed parent.*—Brachycome hybrid cultivar 'Billabong Bright Eyes ', disclosed in U.S. Plant Pat. No. 10,192.

Propagation:

*Type.*—By cuttings.

*Time to initiate roots.*—Summer: About 10 days at temperatures of 25° C. Winter: About 15 days at temperatures of 20° C.

*Time to develop roots.*—Summer: About 15 days at temperatures of 25° C. Winter: About 20 days at temperatures of 20° C.

*Rooting habit.*—Fine, fibrous and freely branching.

Plant description:

*General appearance.*—Compact and outwardly spreading; rounded and mounding; full and dense; herbaceous plant with long peduncles that hold inflorescences above and beyond the foliage. Suitable for 12.5 to 25-cm containers and hanging baskets. To produce a 12.5-cm finished flowering plant from rooted cuttings, about 8 to 12 weeks are required depending on temperature and light level.

*Plant height.*—About 18 cm from soil level to top of inflorescences.

*Plant diameter or spread.*—About 28 cm.

*Branching.*—Very freely branching, pinching is usually not required.

*Growth rate/vigor.*—Vigorous.

*Stem description.*—Quantity of lateral branches: Typically about 23 per plant with numerous secondary and tertiary branches. Lateral branch length: About 28 cm. Lateral branch diameter: About 2 mm. Internode length: About 1.5 to 3 cm. Texture: Glabrous. Color: 143A.

*Foliage description.*—Arrangement: Alternate. Quantity: About 200 per lateral branch. Shape: Deeply dissected; typically seven leaf segments that are further dissected; narrowly oblong; apex, acute; base, attenuate. Length: Typically about 3.5 cm. Width: About 2.75 cm. Margin: Entire. Texture: Smooth. Petiole length: About 7.5 mm. Petiole diameter: About 1.5 mm. Color: Young leaves, upper surface: 143A. Young leaves, lower surface: 143B to 143C. Fully expanded leaves, upper surface: 147A. Fully expanded leaves, lower surface: 147B. Petiole: 138A.

Flowering description:

*Inflorescence.*—Single daisy-type composite inflorescence form. Florets arranged acropetally on a capitulum. Inflorescences held above and beyond the foliage on long peduncles. Inflorescences maintain good color and substance for about 2 to 3 weeks. Inflorescences persistent.

*Natural flowering season.*—Natural flowering season is spring to fall; flowering continuous during this period.

*Quantity of inflorescences.*—Floriferous with typically about 17 open inflorescences and buds per lateral stem; more than 300 open inflorescences and buds per plant.

*Inflorescence diameter.*—About 1.8 cm.

*Inflorescence depth (height).*—About 8 mm.

*Disc diameter.*—About 8 mm.

*Inflorescence aspect.*—Flat.

*Rate of inflorescence opening.*—About 5 to 10 days depending on temperature.

*Fragrance.*—None detected.

*Inflorescence buds.*—Shape: Round to ovate. Length: About 6 mm. Diameter: About 4 mm. Color: 85A.

*Ray florets.*—Quantity: One whorl of about 30 florets per inflorescence. Shape: Ligulate, narrowly oblong. Apex: Rounded or slightly notched. Base: Attenuate. Margin: Entire. Aspect: Flat. Length: About 1 cm. Width: About 1 mm. Texture: Smooth. Color: When opening, upper surface: 90C. When opening, lower surface: 85A. Mature, upper surface: 90B. Mature, lower surface: 85A.

*Disc florets.*—Shape: Tubular with 5-lobed corolla. Length: About 5 mm. Width: About 1 mm. Color: Immature: 1C. Mature: 1A. Number of disc florets per inflorescence: About 40.

*Peduncle.*—Length: Terminal peduncle: About 6.5 cm. Fourth peduncle: About 5 cm. Seventh peduncle: About 4.4 cm. Strength: Flexible, moderate strength. Angle: Acute. Texture: Smooth. Color: 146B.

*Involucral bracts.*—Arrangement: Imbricate, two whorls. Quantity: About 14 per inflorescence. Shape: Mostly elliptic. Apex: Acute. Margin: Entire. Texture: Smooth. Color: Upper surface: 137C. Lower surface: 137A.

*Androecium.*—Stamen number: Five per disc floret. Anther shape: Oblong. Anther size: About 0.5 mm. Anther color: 1B. Amount of pollen: Scarce. Pollen color: 1A.

*Gynoecium.*—Pistil number: One per floret. Stigma shape: Bilobate. Pistil length: About 1.5 mm. Style color: 1C. Stigma color: 1C. Ovary color: 1D.

Disease resistance: Disease resistance to pathogens common to Brachycome has not been observed.

Seed production: Seed production has not been observed.

It is claimed:

1. A new and distinct cultivar of Brachycome plant named 'Compact Amethyst', as illustrated and described.

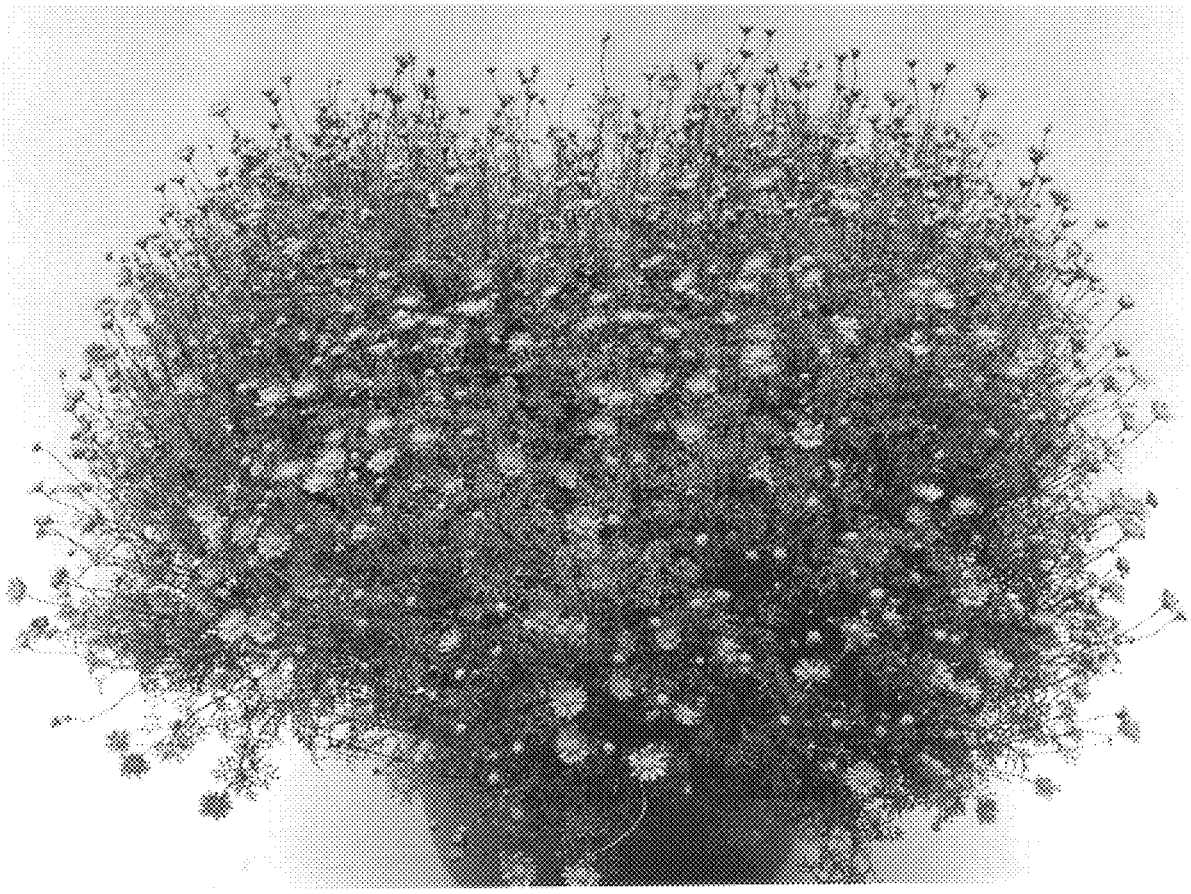

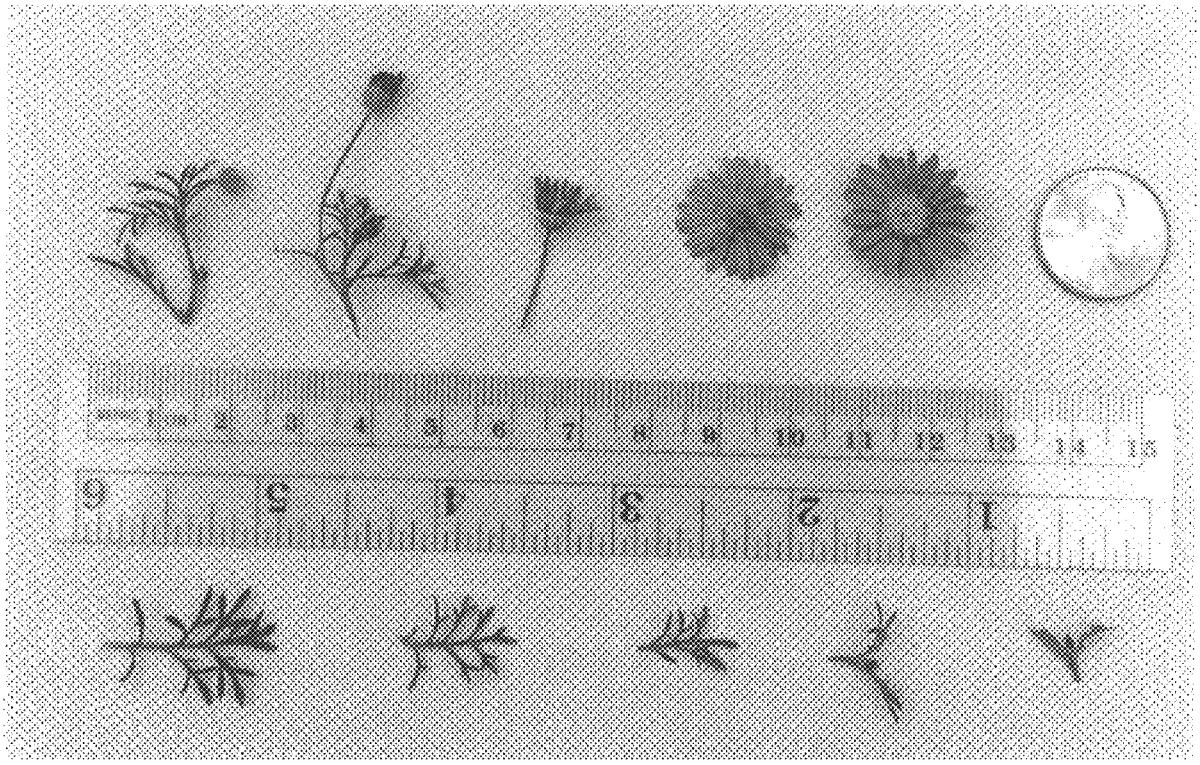

* * * * *